United States Patent [19]

Kovach et al.

[11] 3,998,897

[45] Dec. 21, 1976

[54] SELECTIVE HYDROGENATION OF CYCLOPENTADIENE-NORBORNADIENE MIXTURES

[75] Inventors: Stephen M. Kovach; George D. Wilson, both of Ashland, Ky.

[73] Assignee: Ashland Oil, Inc., Ashland, Ky.

[22] Filed: Dec. 19, 1975

[21] Appl. No.: 642,374

[52] U.S. Cl. .................. 260/666 A; 260/666 PY; 260/677 H
[51] Int. Cl.² .................. C07C 7/00; C07C 13/28
[58] Field of Search ........ 260/666 A, 666 PY, 666, 260/681.5

[56] References Cited

UNITED STATES PATENTS

| | | | |
|---|---|---|---|
| 3,075,917 | 1/1963 | Kronig et al. | 260/681.5 R |
| 3,439,060 | 4/1969 | Kempton | 260/681.5 R |
| 3,565,963 | 2/1971 | Tabler et al. | 260/666 A |
| 3,751,499 | 8/1973 | Tazuma | 260/666 A |

*Primary Examiner*—Veronica O'Keefe
*Attorney, Agent, or Firm*—Van D. Harrison, Jr.

[57] ABSTRACT

2,5-Norbornadiene (bicyclo (2.2.1) hepta-2,5 diene) containing cyclopentadiene as an impurity is purified by selectively hydrogenating the cyclopentadiene to cyclopentane and/or cyclopentene with a palladium-on-alumina catalyst without preceptible hydrogenation of the 2,5-norbornadiene.

6 Claims, No Drawings

SELECTIVE HYDROGENATION OF CYCLOPENTADIENE-NORBORNADIENE MIXTURES

FIELD OF THE INVENTION

This invention relates to the treatment of impure bicyclo (2.2.1) hepta-2,5 diene (2,5-norbornadiene) hereinafter designated simply as norbornadiene. More specifically, it relates to a method for selectively converting cyclopentadiene to cyclopentene and cyclopentane by hydrogenation in the presence of norbornadiene, when the cyclopentadiene occurs as a detrimental impurity in the norbornadiene.

Norbornadiene is prepared commercially by reacting cyclopentadiene with acetylene. The norbornadiene can then be polymerized to make high energy fuels useful as missile propellants. U.S. Pat. Nos. 3,326,992; 3,377,398; and 3,282,663 disclose compositions and processes relating to such polymers that are particularly useful as high energy fuels. The presence of cyclopentadiene as an impurity in the norbornadiene is undesirable in that it forms complexes with the polymerization catalyst and causes high catalyst consumption. Separation of cyclopentadiene from norbornadiene prior to the polymerization step is an extra and expense-creating step. It has been determined, however, that the presence of cyclopentene or cyclopentane in norbornadiene is not particularly detrimental in the polymerization process. It is highly desirable therefore to have a process, preferably continuous, wherein cyclopentadiene present in a fluid stream of norbornadiene can be hydrogenated to cyclopentene and cyclopentane without appreciable consumption of norbornadiene. A primary object of this invention is to provide such a process.

SUMMARY OF THE INVENTION

Briefly stated, this invention comprises contacting a fluid stream of norbornadiene containing cyclopentadiene as an impurity with hydrogen in the presence of a catalyst consisting essentially of palladium on an alumina catalyst under suitable conditions of pressure, temperature and liquid space velocity thereby converting the cyclopentadiene to cyclopentene and cyclopentane.

DETAILED DESCRIPTION OF THE INVENTION

The preferred catalyst for carrying out the process of this invention is one consisting essentially of palladium in elemental form supported on an alumina carrier. Preferably the amount of elemental palladium present in the catalyst is between 0.1 and 0.5 percent by weight although higher concentrations of palladium up to 2 percent can be used.

Although other supports of neutral or basic character can be used, the preferable support is a high surface area-alumina, such as the beta, eta, and gamma alumina forms, bayerite, and boehmite. Catalysts which can be used in the process of this invention are available commercially under such tradenames as Harshaw 0501 (Harshaw Chemical Company) and Gridler G68 (Gridler Chemical Company). Supports of an acid nature are not desirable because they promote plugging of the support.

The process is carried out peferably by flowing a feedstock of the impure liquid norbornadiene through or over a bed of the aforedescribed palladium-on-alumina catalyst. At the same time, gaseous hydrogen is also flowed through the catalyst bed concurrently or countercurrently so that the liquid feedstock and hydrogen gas are intimately contacted. The liquid effluent recovered from the catalyst bed is the desired product, that is liquid norbornadiene in which the amount of cyclopentadiene contaminant has been substantially reduced. Depending upon the degree of hydrogenation of cyclopentadiene desired, the liquid effluent norbornadiene can be partially recycled or can be sent on to the polymerization process. The gaseous effluent from the catalyst bed can be processed or recycled accordingly, to the desire of the operator. The process is conducted at temperatures between about 200° F. and about 500° F., a pressure of about 100 to 1,000 psig, a liquid space velocity of about 0.5 to about 5 volumes of liquid feedstock per volume of catalyst per hour and at a ratio of hydrogen gas to liquid feedstock of about 50 to about 500 standard cubic feet of (60° F. and 1 atmosphere) per barrel of feedstock. For purposes of measuring the liquid hourly space velocity and hydrogen gas/liquid feedstock ratios, the volume of liquid feedstock entering the process is metered at some point just prior to entering the zone of contact between feedstock, hydrogen gas and catalyst.

The liquid effluent stream removed from the contact zone will contain essentially no cyclopentadiene. The cyclopentadiene originally present will have been converted to cyclopentene and/or cyclopentane. Because these hydrocarbons do not interfere with subsequent polymerization of norbornadiene, they need not be removed prior to a polymerization step. At some later step, in the purification of the polymer, the cyclopentene and cyclopentane can be removed by fractionation or other means.

EXAMPLE 1

In a series of runs with two different catalysts, norbornadiene containing 3210 ppm (0.32 percent by weight) of cyclopentadiene was treated according to the process of this invention at three temperature levels, all tests being conducted at 400 psig. Details and results of the test runs are tabulated below.

| Run No. | 1 | 2 | 3 | 4 | 5 | 6 |
|---|---|---|---|---|---|---|
| Catalyst | | 0.3% Pd on Alumina (1) | | | 0.5% Pd on Alumina (2) | |
| Temperature of Hydrogenation | 250° F. 121 C. | 325° F. 163 C. | 400° F. 204 C. | 250° F. 121 C. | 325° F. 163 C. | 400° F. 204 C. |
| Liquid Hourly Space Velocity | & 1 | & 1 | & 1 | & 1 | & 1 | & 1 |
| Hydrogen to Feedstock Ratio (3) | 50 | 50 | 50 | 50 | 50 | 50 |
| Analysis of Liquid Effluent, Percent by weight | | | | | | |

-continued

| Run No. | 1 | 2 | 3 | 4 | 5 | 6 |
|---|---|---|---|---|---|---|
| Catalyst | 0.3% Pd on Alumina (1) | | | 0.5% Pd on Alumina (2) | | |
| Cyclopentadiene | 0.24 | 0.19 | 0 | 0.17 | 0.1 | 0.008 |
| Norbornadiene, Cyclopentene and Cyclopentane | 99.76 | 99.81 | 100.0 | 99.83 | 99.9 | 99.992 |
| Percent Conversion of Cyclopentadiene | 25 | 41 | 100 | 47 | 69 | 98 |

(1) Harshaw 0501
(2) Baker Chemical Company
(3) SCF of Hydrogen (60° F. and 1 atmosphere) per bbl of Feedstock In This Example there was no perceptible loss of norbornadiene resulting from hydrogenation

EXAMPLE 2

In another test, the catalyst of Runs 1–3 was used to purify a norbornadiene of the composition of Example 1 at a temperature of 400° F. (204° C.), a pressure of 400 psig, a liquid hourly space velocity of 1, and a hydrogen to feedstock ratio of 140 cubic feet of hydrogen (60° F. and 1 atmos.) per barrel of feedstock. The effluent stream was monitored over a period of time for cyclopentadiene content with the results shown below.

| Percent by weight of cyclopentadiene remaining in effluent stream after | |
|---|---|
| 8 hours | .041 |
| 16 hours | .041 |
| 24 hours | — |
| 36 hours | .032 |

Analysis of the effluent stream did not indicate any perceptible loss of norbornadiene by hydrogenation.

From the foregoing data it will be readily apparent that the process of this invention results in a selective hydrogenation of the cyclopentadiene present in a norbornadiene-cyclopentadiene mixture without any appreciable loss of norbornadiene, yielding a product which can then be directly used in a process for polymerizing the norbornadiene.

We claim:

1. A process for selectively hydrogenating cyclopentadiene present in a liquid cyclopentadiene-norbornadiene mixture comprising contacting said mixture with hydrogen gas in the presence of a catalyst consisting essentially of palladium on an alumina support under conditions sufficient to cause hydrogenation of substantially all of said cyclopentadiene to cyclopentene and/or cyclopentane and substantially none of said norbornadiene.

2. The process of claim 1 wherein said cyclopentadiene-norbornadiene mixture comprises up to 1 percent by weight of cyclopentadiene.

3. The process of claim 1 wherein said catalyst consists essentially of between about 0.1 and about 2 percent by weight of palladium on an alumina support.

4. The process of claim 3 wherein the alumina is selected from the group consisting of beta, eta, and gamma alumina, bayerite and boehmite.

5. The process of claim 1 wherein said hydrogenation is conducted at a temperature of between about 200° and about 500° F. and at a pressure of between about 100 psig. and about 1,000 psig.

6. The process of claim 1 wherein said cyclopentadiene-norbornadiene mixture comprises up to 1 percent by weight of cyclopentadiene, said catalyst consists essentially of between about 0.1 and about 2 percent by weight of elemental palladium on an alumina support, and said hydrogenation is conducted at a temperature between about 200° and about 500° F., a pressure of about 100 to about 1,000 psig., a liquid hourly space velocity of about 0.5 to about 5, and a ratio of hydrogen gas to liquid mixture of about 50 to 500 scf per barrel of liquid.

* * * * *